(12) United States Patent
Thorn et al.

(10) Patent No.: US 7,803,153 B2
(45) Date of Patent: Sep. 28, 2010

(54) METHOD FOR PREVENTING MYOPIA PROGRESSION THROUGH IDENTIFICATION AND CORRECTION OF OPTICAL ABERRATIONS

(75) Inventors: Frank Thorn, Newton, MA (US); Richard Held, Cambridge, MA (US); Jane E. Gwiazda, Brookline, MA (US); Ji C. He, Somerville, MA (US)

(73) Assignee: New England College of Optometry, Boston, MA (US)

( * ) Notice: Subject to any disclaimer, the term of this patent is extended or adjusted under 35 U.S.C. 154(b) by 1228 days.

(21) Appl. No.: 10/169,418

(22) PCT Filed: Dec. 28, 2000

(86) PCT No.: PCT/US00/35582
§ 371 (c)(1),
(2), (4) Date: Oct. 2, 2002

(87) PCT Pub. No.: WO01/47449
PCT Pub. Date: Jul. 5, 2001

(65) Prior Publication Data
US 2003/0058404 A1    Mar. 27, 2003

Related U.S. Application Data

(60) Provisional application No. 60/173,582, filed on Dec. 29, 1999.

(51) Int. Cl.
*A61B 18/18* (2006.01)
(52) U.S. Cl. .......................................................... 606/5
(58) Field of Classification Search .................. 351/205, 351/206, 211, 212, 219, 221; 606/1, 4, 5; 128/898; 623/898, 6.11; 359/618, 615
See application file for complete search history.

(56) References Cited

U.S. PATENT DOCUMENTS

| 4,579,430 A | 4/1986 | Bille ........................... 351/206 |
| 4,923,467 A * | 5/1990 | Thompson .................. 128/898 |
| 5,130,843 A | 7/1992 | He et al. ..................... 359/285 |
| 5,815,239 A | 9/1998 | Chapman et al. ............ 351/177 |
| 5,937,113 A | 8/1999 | He et al. ....................... 385/11 |
| 6,002,484 A | 12/1999 | Rozema et al. ............. 356/354 |

(Continued)

FOREIGN PATENT DOCUMENTS

WO        WO 98/25174       6/1998

OTHER PUBLICATIONS

Noll, R. J. *Zernike polynomials and atmosfpheric turbulence*, Journal of Optical Society of America, (1975), retrieved Dec. 27, 1999 at http://lest.fys.dtu.dk/Results/Zernike_polynomials.htm.

(Continued)

*Primary Examiner*—George Manuel
(74) *Attorney, Agent, or Firm*—Sunstein Kann Murphy & Timbers LLP

(57) ABSTRACT

A method for at least one of preventing myopia and retarding the progression of myopia is provided. The method includes measuring optical aberrations in a human eye (42, 43, 44) and correcting the optical aberrations (46). Measuring optical aberrations (42, 43, 44) may include measuring wavefront aberrations (45) of parallel light rays entering the eye.

34 Claims, 4 Drawing Sheets

U.S. PATENT DOCUMENTS

| | | | | |
|---|---|---|---|---|
| 6,038,067 | A | * | 3/2000 | George ........................ 359/368 |
| 6,045,578 | A | | 4/2000 | Collins et al. ................... 623/6 |
| 6,050,687 | A | | 4/2000 | Bille et al. ................... 351/212 |
| 6,270,221 | B1 | * | 8/2001 | Liang et al. ................. 351/221 |

OTHER PUBLICATIONS

Gwiazda, J., et al. *Myopic Children Show Insufficient Accommodative Responsive to Blur*, Investigative. Ophthalmology & Visual Science, Mar. 1993, pp. 690-694, vol. 34, No. 3.

Atchison, David, *Aberrations Associated with Contact Lenses*, Vision Science and Its Applications Meeting, 1994 Proceedings.

Bartsch, et al. *Resolution Improvement in Confocal Scanning Laser Tomography of the Human Fundus*, Technical Digest Series 2, Optical Society of America, Optical Society of America, 1994, pp. 134-137, 2.

Liang, J., et al., *Objective measurement of wave aberrations of the human eye with the use of a Hartmann-Shack wave-front sensor*, Optical Society of America, Jul. 1994, pp. 1949-1957, vol. 11, No. 7.

Gwiazda, J., et al., *A Dynamic Relationship between Myopia and Blur-Driven Accommodation in School-aged Children*, Vision Res., 1995, pp. 1299-1304, vol. 35, No. 9.

Thorn, F., et al. *Myopia Adults See Through Defocus Better Than Emmetropes*, Myopia Updates, Springer, Tokyo, Spring/Summer 1998, pp. 368-374, T. Tokoro (ed.).

He, J. C., et al. *Measurement of the wave-front aberration of the eye by a fast psychophsical procedure*, Journal of Optical Society of America, Sep. 1998, pp. 2449-2456, vol. 15, No. 9.

Chateau, N., et al. *Influence of myopia and aging on the optimal spherical aberration of soft contact lenses*, Journal of Optical Society of America, Sep. 1998, pp. 2589-2596, vol. 15, No. 9.

Gwiazda, J., et al. *Response AC/A ratios are elevated in myopic children*, Physiol. Optics, 1999, pp. 173-179, vol. 19, No. 2.

Rosenfield, M., et al. *Blur Sensitivity in Myopes*, Optometry and Vision Science, May 1999, pp. 303-307, vol. 76, No. 5.

Leung, J., et al. *Progression of Myopia in Hong Kong Chinese Schoolchildren Is Slowed by Wearing Progressive Lenses*, Optometry and Vision Science, Jun. 1999, pp. 346-354, vol. 76, No. 6.

Pacella, R., et al., *Role of Genetic Factors in the Etiology of Juvenile-Onset Myopia Based on a Longitudinal Study of Refractive Error*, Optomtometry and Vision Science, Jun. 1999, pp. 381-386, vol. 76, No. 6.

He, J., et al., *High optical quality is a necessary condition for the human eye to maintain emmetropia*, (1999).

He, J., et al., *Monochromatic aberrations in the accommodated human eye*, Vision Research, 1999, pp. 1-8.

Atchison, et al., *Mathematical Treatment of Ocular Aberrations: a User's Guide*, Vision Science and Its Applications, 2000, pp. 110-130, vol. 35.

Campbell, M. *Contributions to the Optical Quality of the Eye: Implications for "Perfect" Optical Correction*, Vision Science and Its Applications, 2000, pp. 131-139, vol. 35.

Roorda, A., *Adaptive Optics and Retinal Imaging*, Vision Science and Its Applications, 2000, pp. 151-162, vol. 35.

Thibos, L., *Principles of Hartmann-Shack Aberrometry*, Vision Science and Its Applications, 2000, pp. 163-169, vol. 35.

Hamam, H. *A quick method for analyzing Hartmann-Shack patterns: application to corneal surgery*, Vision Science and Its Applications, 2000, pp. 187-198, vol. 35.

Hong, X., et al. *Optical Aberrations Following Laser in Situ Keratomileusis (LASIK) Surgery*, Vision Science and Its Applications, 2000, pp. 220-226, vol. 35.

Munger, R. *New paradigm for the treatment of myopia by refractive surgery*, Vision Science and Its Applications, 2000, pp. 227-230, vol. 35.

Thibos, L., et al. *Standards for Reporting the Optical Aberrations of Eyes*, Vision Science and Its Applications, 2000, pp. 232-244, vol. 35.

Guirao, A., et al. *Effect of Rotation and Translation on the Expected Benefit of Ideal Contact Lenses*, Vision Science and Its Applications, 2000, pp. 324-329, vol. 35.

International Search Report for International application No. PCT/US00/35582, under mailing date of Jun. 6, 2001.

* cited by examiner

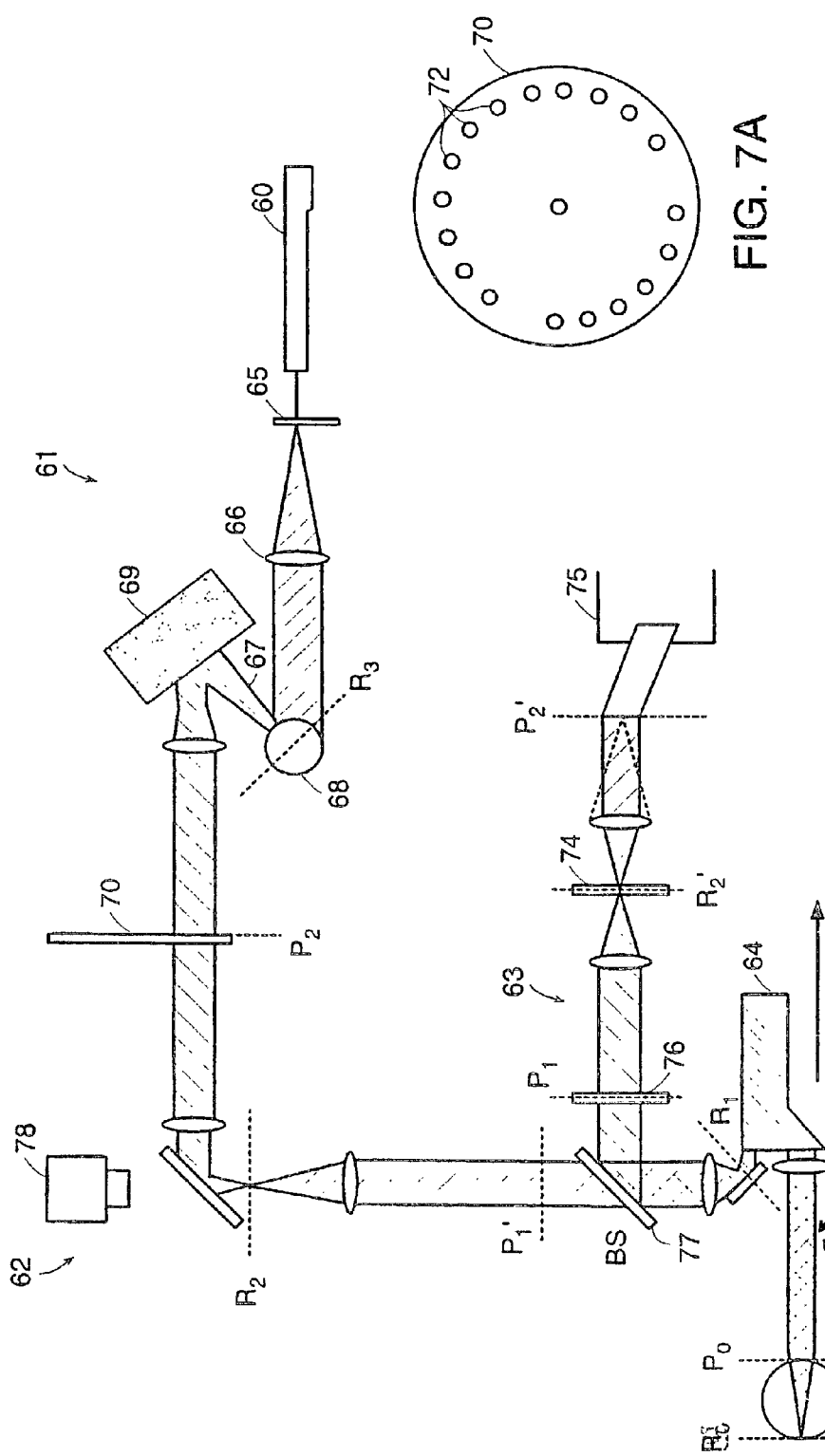

METHOD FOR PREVENTING MYOPIA PROGRESSION THROUGH IDENTIFICATION AND CORRECTION OF OPTICAL ABERRATIONS

TECHNICAL FIELD

The present invention pertains to measuring optical aberrations in the human eye and, more particularly, to preventing myopia and retarding the progression of myopia by correcting the aberrations.

BACKGROUND ART

Myopia (or near-sightedness) has become the most pervasive visual disorder in the world. About twenty-five percent of people in industrialized countries in the Western world, and more than fifty percent of people in industrialized Asian countries require optical correction for myopia. With increasing educational demands, the prevalence of myopia is increasing steadily. Extensive reading by children and adolescents appears to cause progressive myopia. Since increasing educational demands have increased the prevalence of myopia, optical correction, such as eyeglasses, contact lenses, and refractive surgery for myopia is a major health care expense.

Myopia is due primarily to an elongation of the posterior pole of the eye during the school age years. Structures in this region of the eye tend to be stretched during development, and their integrity is compromised. This causes greater risk to the effects of ocular trauma, diabetes, macular degeneration, and other diseases. This means that myopia is also a major contributor to irreversible blindness.

Referring to FIG. 1, in a normal eye, the cornea 10 and lens 12 at the front of the eye focus an image of the visual world on the retinal receptors 14 at the back of the eye. At the retinal receptors the image begins to be processed and sent on to the brain as a complex neural signal. A myopic eye is too long, so that the image of most of the visual world is focused in front of the retina. Consequently, myopia is treated by weakening the optical power in the front of the eye so that the image is focused on the retina. This means that eyeglasses, contact lenses and refractive surgery are not treating the basic disorder, but are merely counteracting the effects of ocular elongation. Each of these treatments has its own problems, is expensive, and in no way reduces the likelihood that the myopic person will contract one of the blinding diseases which are secondary to myopia later in life.

Eyeglasses, contact lenses, and to a lesser extent, refractive surgery can accurately correct myopic defocus (often referred to as the spherical error of the eye) by placing as much of the focused image as possible on the retina. Some eyes have an aberration that creates a difference in optical power between one meridional orientation and another. This aberration is known as astigmatism and is correctable with eyeglasses (although eyeglasses cause visual distortion) and with specialty contact lenses (which may be uncomfortable).

At least thirty other "higher order" aberrations can be measured and quantified in the human eye. Each of these aberrations contributes a different type of degradation to the retinal image. These aberrations are usually measured in the laboratory with a complex optical instrument in which a laser beam is aimed at the retina of people who have their pupils dilated with drugs. However, such aberrations can now be measured in children and adolescents without the use of bright light or the need for pupillary dilation with drugs.

Traditional clinical correction of optical defocus places the average position of an image of the visual world on the retina. However, parts of that image may be in front of or behind the retina due to the refractive properties of the eye's aberrations. Thus, most of the image in a "perfectly" corrected eye may be significantly out of focus due to these aberrations.

A small number of people have myopia due to rare inherited diseases or, in old age, in conjunction with diabetic crystalline lens changes. More than ninety percent of the people with myopia, however, develop it during their school age years. It has been shown that this progressive myopia is clearly related to a genetic predisposition (Pacella et al., "*Role of Genetic Factors in the Etiology of Juvenile-Onset Myopia Based on a Longitudinal Study of Refractive Error*," Optom. Vis. Sci. 76, 381-386, (1999)) and to an intensity of school work, especially reading.

Animal studies have shown conclusively that blurring the visual world by scattering an image through the use of eyelid closure or smoked or sandblasted eyeglass lenses leads to myopia. Similarly, defocusing the visual world with minus lenses induces myopic response. Both blurring (i.e., general image degradation) and myopigenic defocus affects myopigenesis more in some species than in others and more in some breeds than in others within the same species. This suggests that the myopic response to environmental influences is genetically dependent.

Epidemiological studies and other studies demonstrate the same type of environmental-genetic interaction

SUMMARY OF THE INVENTION

A method is provided for preventing myopia and/or retarding the progression of myopia by measuring optical aberrations in a human eye and correcting the optical aberrations.

In accordance with one embodiment of the invention, the step of measuring includes measuring wavefront aberrations of parallel light rays entering the eye. The step of measuring may also include measuring deviations at the retina of parallel light rays entering the eye, as well as measuring deviations at the pupil of parallel light rays entering the eye.

In accordance with another embodiment of the invention, the step of measuring may include providing a multi-channel optical system wherein an aperture is moved to multiple positions with respect to the pupil of the eye and alignment parameters for each aperture position is recorded at least one optical distance. A system of equations is then solved to derive a set of aberration constants based on the alignment parameters. The step of measuring may also include detecting first and higher order astigmatism and/or detecting at least one of first and higher order coma, spherical aberrations and other aberrations.

In accordance with a further embodiment of the invention a method for preventing myopia and/or retarding the progression of myopia includes screening for aberrations in a human eye, measuring the aberrations and correcting the aberrations. The step of screening may include detecting a depth of focus by measuring visual acuity, contrast sensitivity and/or blur sensitivity and the visual acuity, contrast sensitivity and/or blur sensitivity may be measured with a psycho-physical test.

In accordance with other embodiments of the invention, the step correcting may include providing an optical device, providing at least one optical lens and/or providing at least one contact lens. The step of correcting may also include altering an optical surface in the eye and/or performing corneal surgery. The step of correcting may further include providing intra-ocular implants.

In accordance with additional embodiments of the invention, the step of correcting includes providing adaptive optics, and the adaptive optics may include deformable mirrors, systems of multiple lenslettes, micro-mirror electro-machined components, optically addressed liquid crystal spatial light modulators, membrane mirrors, and/or piezoelectric bi-morph mirrors. The adaptive optics may produce periods of clear vision and may be miniaturized so as to be wearable on the face of a person The step of correcting may also include providing high illumination levels to reduce the pupil of the eye.

BRIEF DESCRIPTION OF THE DRAWINGS

FIG. 6 is a schematic of a multi-channel optical device that may be used to perform the measurements of the present invention;

FIG. 7A shows a front view of a prior art pupil sampling aperture; and

FIG. 7B shows a pattern of entry positions at the pupil of the subject of a sampling beam using the apparatus of FIG. 7A.

DETAILED DESCRIPTION OF SPECIFIC EMBODIMENTS

The inventors have shown that myopic children and adolescents tend to under accommodate when looking at near targets during and prior to the period in which they are developing myopia. This under accommodation results in a myopigenic defocus similar to that which induces myopia in animal experiments. The inventors have also demonstrated that children and adolescents who are becoming myopic have certain binocular anomalies (near esophoria and high AC/A ratio) which tend to cause under accommodation (Gwiazda, J., Thorn, F., Bauer, J. and Held, R., "*Myopia Children Show Insufficient Accommodation to Blur*," Invest. Ophthalmol. Vis. Sci., 34, 690-694 (1993); Gwiazda, J., Bauer, J., Thorn, F., and Held, R., "*A Dynamic Relationship Between Myopia and Blur-Driven Accommodation in School Aged Children*," Vision Res., 35, 1299-1304 (1995); Gwiazda, J., Grice, K., and Thorn, F., "*Response AC/A Ratios are Elevated in Myopic Children*," Physiol. Optics., 19, 173-179 (1999) all of which are incorporated herein be reference). This suggests that myopigenic defocus due to under-accommodation induces myopia in children and adolescents.

When children must look intensely at near patterns, for example, during reading, their eyes accommodate (focus) and converge (turn in together) on the text being read. This accommodation effort tends to increase optical aberrations, causing increased blur, and the eyes tend to under accommodate, causing a myopigenic defocus. These innate factors, plus extensive reading in children and adolescents whose eyes are still young enough to grow, appear to cause progressive myopia.

The inventors have shown that all adults with high amounts of optical aberrations are myopic. In fact, about 25% of myopic children and adults have optical aberrations that are greater that those in non-myopic adults. The aberrations in myopic eyes were often two or three times as large as the upper limit in non-myopic adults.

In accordance with the present invention, it is taught that if large aberrations in the eyes of children are detected and treated, the progression of myopia may be retarded or eliminated.

Definitions and proposed standards relating to measurement of optical aberrations are available in (Atchison et al., "*Mathematical Treatment of Optical Aberrations: A User's Guide*," Trends in Optics and Photonic, Optical Society of America, 35, 110-130 (2000) and Thibos et al., "*Standards for Reporting the Optical Aberrations of the Eyes*," Trends in Optics and Photonics, Optical Society of America, 35, 232-244 (2000) which are hereby incorporated herein by reference.

Figure 2:
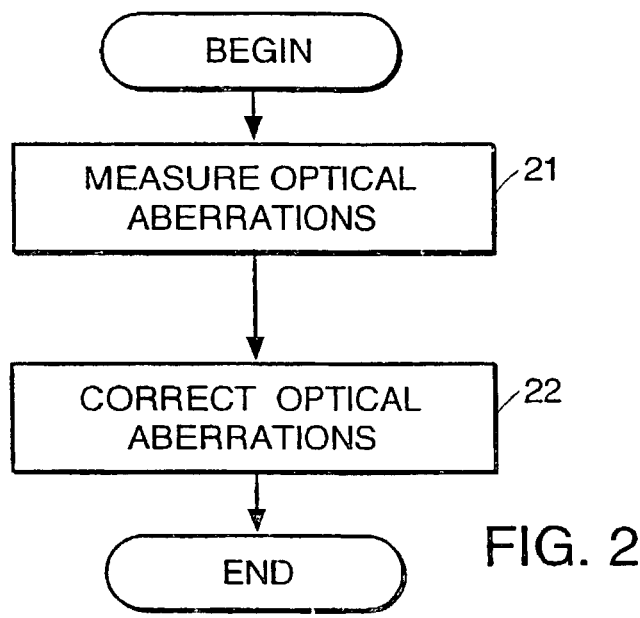
FIG. 2 is a flow chart representing the steps involved in a method of the present invention.

FIG. 2 illustrates a method for preventing myopia and/or retarding the progression of myopia. Optical aberrations are measured in step 21. Aberrations may be expressed in terms of Zernike polynomials; however, the use of other representations is within the scope of the invention. The optical aberrations are then corrected in step 22 using optical correcting devices well known in the art including, but not limited to, spectacles, contact lenses, adaptive optics, corneal surgery, laser surgery, and intra-ocular implants.

Figure 3:
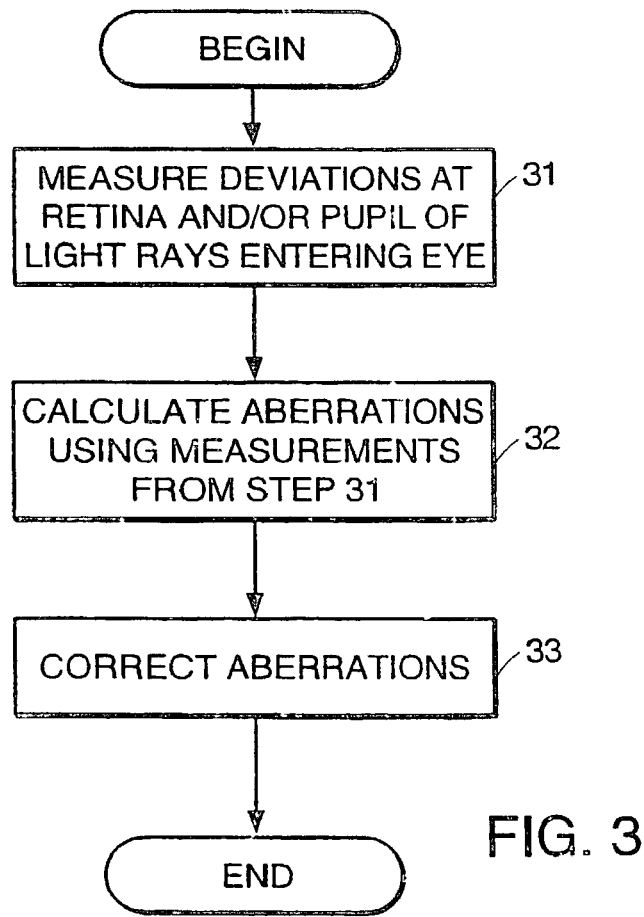
FIG. 3 is a flow chart representing another embodiment of the present invention.

FIG. 3 illustrates a method for preventing myopia and/or retarding the progression of myopia wherein deviations, at a pupillary or retinal location, of parallel light rays (e.g., 16 in FIG. 1) entering a human eye are measured in step 31. The optical aberrations are then calculated, step 32, from the measurements taken in the previous step and the aberrations are corrected in step 33 with optical correction devices as described in connection with FIG. 2.

Figure 4:
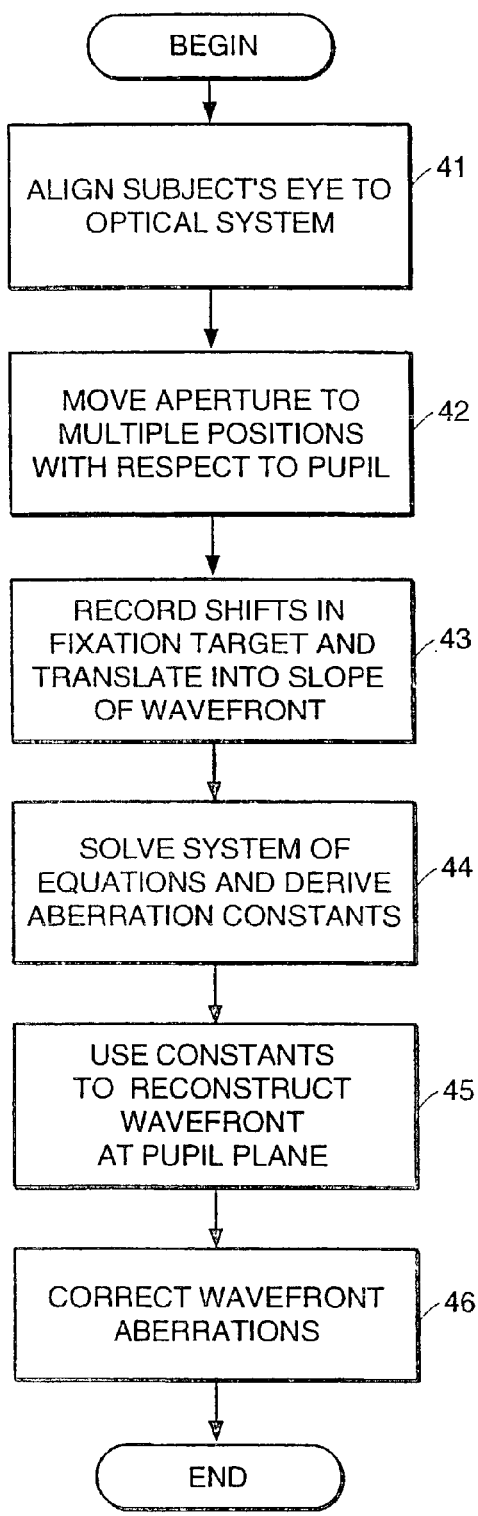
FIG. 4 is a flow chart representing an embodiment of the invention that employs an apparatus such as a multi-channel optical device.

FIG. 4 illustrates a procedure for measuring wavefront aberrations using a three channel system as shown in FIG. 6. The procedure is discussed in He et al., "*High Optical Quality is a Necessary Condition for the Human Eye to Maintain Emmetropia*," (1999), which is attached hereto and incorporated herein by reference. Referring to FIG. 6, the system has separate channels 61, 62, 63 for test, fixation-stimulus, and pupil-monitoring respectively. A pupil of a subject is located at $P_0$ and a retina of the subject is located at $R_0$. A Badal optometer (focusing block) 64 allows an operator to change the refractive state of the test channel 61 and the pupil-monitoring channel 62 together, without changing the location of the pupil conjugate planes ($P_1$, $P_1'$, $P_2$ and $P_2'$) and retinal conjugate planes ($R_1$, $R_2$, $R_2'$, and $R_3$)

A 543-nm He—Ne laser 60 produces light for the test channel 61. The coherence of the laser 60 is broken by a rotating diffuser 65. The light from the laser 60 is collimated by a lens 66 and 12 mm steel ball 68. The reflection from the ball 68 produces a divergent, high-numerical aperture beam 67 that the subsequent optics image as a point source. A gimbaled mirror 69 is controlled by an analog joystick (not shown) that allows the subject to change the angle of the mirror 69 rapidly in two dimensions. Tilting the mirror 69 changes the angle at which the test beam enters the eye and therefore changes the retinal location of the test spot.

At the pupil-monitoring channel 62, a pupil entry position of the test beam is selected from a set of 1 mm holes 72 (shown in FIG. 7A) that tile the pupil of the eye by rotating a aperture metal wheel 70 (see FIG. 7A) that is optically conjugate to the pupil. The aperture wheel 70 is constructed such that it can be rotated to one of 37 preset locations.

A fixation target, typically a cross, is provided at a fixation-stimulus channel 63. The fixation-stimulus channel 63 is illuminated by a light source, such as a fiber-optic illuminator 75. Light from the illuminator 75 is collimated and then passes through a filter holder-slide holder 74 located in a retinal conjugate plane $R_2'$. The light from the illuminator 75 is then imaged on an adjustable iris diaphragm 76 located in a pupil conjugate plane $P_1$. The iris diaphragm 76 is set to 1 mm diameter to match the size of the pupil sampling. However, for conditions in which the wavefront properties of the eye are measured when the eye is accommodated by high illumination levels, the diameter is increased to 6 mm to provide a better stimulus. The fixation-stimulus channel 63 is combined with the pupil-monitoring channel 62 at beam splitter 77.

In step 41 of FIG. 4, the subject's eye is first aligned to the optical axis of the system by using an infrared sensitive CCD video camera 78. The camera 78 provides a magnified view of the pupil. By looking at a monitor screen of a computer (not shown) and adjusting the Badal system 64 to clarify the screen, the eye is at its resting state. Measurements are referenced to the entry location within the pupil. The measurements consist of a few practice trials and six tests, three for each eye. In step 42 an aperture 72 is moved to multiple positions with respect to the pupil to produce a pattern as shown in FIG. 7B. A test may consist of thirty-nine trials with the first and the last trials for the center of the pupil. The other thirty-seven trials randomly sample the entire pupil with a 7×7 matrix in 1 mm steps except the twelve points in the four corners. The subject's task is to align a cursor with the center of the fixation target and click a mouse of the computer on each trial. Each test usually lasts about three minutes, and the entire session requires approximately thirty minutes.

In step 43, the shifts in the fixation target are recorded by the computer and translated into the slope of the wavefront at the thirty-seven pupil locations. In step 44 a system of equations is solved using a least square procedure to fit the slope measurements to the derivative of thirty-five terms of the Zernike polynomial functions. The derived coefficients provide estimates of the weights of the individual aberrations, and are used, in step 45, to reconstruct the overall wavefront at the pupil plane. The aberrations are corrected in step 46 in the same manner as described in step 22 of FIG. 2.

Procedures and devices for measuring wavefront aberrations are further discussed in Liang et al., "*Objective Measurement of Wave Aberrations of the Human Eye With the Use of a Hartmann-Shack Wave-Front Sensor*," Journal of the Optical Society of America A, 11, 1-9 (1994); Thibos, "*Principles of Hartmann-Shack Aberrometry*," Trends in Optics and Photonics, Optical Society of America, 35, 163-169 (2000); and He et al, "*Measurement of the Wave-Front Aberration of the Eye by a Fast Psychophysical Procedure*," Journal of the Optical Society of America A, 15, 2449-2456 (1998) each of which is incorporated herein by reference.

Figure 5:
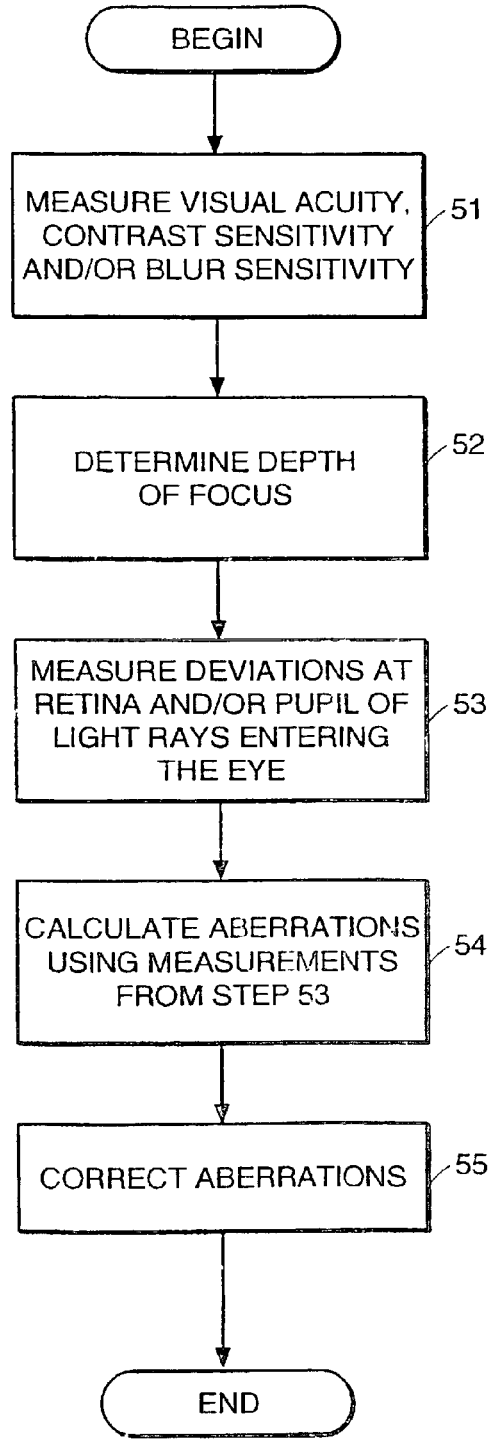
FIG. 5 is flow chart representing an embodiment of the invention wherein aberrations of a human eye are screened by determining depth of focus.

FIG. 5 illustrates a method for retarding the progression of myopia wherein a human eye is screened for aberrations. Visual acuity, contrast sensitivity, and/or blur sensitivity are measured in step 51. Depth of focus is determined in step 52 from the measurements performed in step 51 using procedures described in Thorn et al., "*Myopia Adults See Through Defocits Better than Emmetropes*," Myopia Updates, Springer, Tokyo, 368-374, T. Tokoro (ed.) (1998) and Rosenfield and Abraham-Cohen, "*Blur Sensitivity in Myopes*," Optometry and Vision Science, 76, 303-307 (1999) which are also incorporated herein by reference. Deviations in parallel light rays (e.g., 16 in FIG. 1) entering a human eye at the retina or pupil of the eye are measured in step 53. Aberrations are then calculated, step 54, from the measurements taken in the previous step. The aberrations are precisely measured as described above and then corrected in step 55.

Optical correction for aberrations within the human eye may be provided through several different optical procedures. In one embodiment of the invention, spectacle lenses are used to reduce astigmatic aberrations. In another embodiment of the invention, contact lenses are used to reduce second and third, and perhaps higher orders of aberrations because contact lenses move with the eye, thereby preserving the alignment of their optical surfaces with the optical surfaces of the eye during eye movements. See, (Bartsch et al., "*Resolution Improvement in Confocal Scanning Laser Tomography of the Human Fundus*," Technical Digest Series 2, Optical Society of America, 2, 134-137 (1994) and Guirao et al, "*Effect of Rotation and Translation on the Expected Benefit of Ideal Contact Lenses*," Trends in Optics and Photonics, Optical Society of America, 35, 324-329 (2000) which are incorporated herein by reference.

Lenses may also be used to change (usually reduce) optical accommodation levels in order to reduce optical aberrations. Several studies have used this procedure for various purposes. See, for example, tine study by Jackson and Brown, "*Progression of Myopia in Hong Kong Chinese School Children is Slowed by Wearing Progressive Lenses*," Optometry and Vision Science, 76, 346-354 (1999) which is incorporated herein by reference.

It is also within the scope of the invention to perform corneal surgery to reduce optical aberrations. This procedure is described in Hamam, "*A Quick Method for Analyzing Hartmann-Shack Patterns: Application to Corneal Surgery*," Trends in Optics and Photonics, Optical Society of America, 35, 187-198 (2000); Hong and Thibos, "*Optical Aberrations Following Laser in Situ Keratomileusis (LASIK) Surgery*," Trends in Optics and Photonics, Optical Society of America, 35, 220-226 (2000); and Munger, "*New Paradigm for the Treatment of Myopia Refractive Surgery*," Trends in Optics and Photonics, Optical Society of America, 35, 227-230 (2000) all of which are incorporated herein by reference.

Further, intra-ocular implants a may be used to reduce optical aberrations. The rationale, measurement, and analysis used for the intra-ocular implant embodiment is the same as that in the refractive surgery reduction of aberrations discussed above.

In another embodiment adaptive optics are used to reduce optical aberrations. Adaptive optics may employ deformable mirrors, micro-mirror electro-machined components, lenslette arrays, optically addressed liquid crystal spatial light modulators, membrane mirrors, or piezoelectric bi-morph mirrors to correct the eye's aberrations. Adaptive optics may be used in devices that can be worn when they are miniaturized to the point of wearability. Adaptive optics devices may also be used in instruments that allow patients to experience periods of clear vision through reduced optical aberrations. See, for example, Roorda and Williams, "*Adaptive Optics and Retinal Imaging*," Trends in Optics and Photonics, Optical Society of America, 35, 151-162 (2000) and Munger, "*New Paradigm for the Treatment of Myopia Refractive Surgery*," Trends in Optics and Photonics, Optical Society of America, 35, 227-230 (2000) each of which is incorporated herein by reference.

In another embodiment high illumination levels are used to reduce pupil size thereby reducing the amount of optical aberrations. This method is discussed in Campbell, "*Contributions to the Optical Quality of the Eye: Implications for 'Perfect' Optical Correction*," Trends in Optics and Photonics, Optical Society of America, 35, 227-230 (2000) which is also incorporated herein by reference.

It should also be noted that the embodiments described herein are not mutually exclusive and can be used in combination. For example, visual acuity, contrast sensitivity and/or blur sensitivity may be measured in combination with measurement of wavefront aberrations. Likewise, the numerous devices mentioned above in connection with correcting the aberrations may be used in combination with one another to produce equivalent or superior results.

Although the above embodiments are preferred, many modifications and refinements which do not depart from the true spirit and scope of the invention may be conceived by those skilled in the art. It is intended that all such modifications, including but not limited to those set forth above, be covered by the following claims.

High Optical Quality is a Necessary Condition for the Human Eye to Maintain Emmetropia Ji C. He*, Pei Sun§, Richard Held*, Frank Thorn*, Editha Ong*, Xiuru Sun§, Jane E. Gwiazda*

*New England College of Optometry, 424 Beacon Street, Boston, Mass. 02115, USA

§ Institute of Psychology, Chinese Academy of Science, P.O. Box 1603, Beijing, Beijing 100012, P. R. China Vision is optimized when the focal plane of the eye's optics is coincident with the retina so that the image of a distant object falls on the photoreceptor layer: a condition called emmetropia. A mismatch between the focal and axial lengths of the eye causes refractive errors in the forms of either hyperopia (far-sightedness), when the focal plane lies behind the retina, or myopia (near-sightedness), when it is in front of the retina. Most children's eyes approach emmetropia at about 5 years of age from a mismatch in infancy[1-2]. While many children maintain their emmetropia into adulthood, others become myopic because the eye rows too long. Animal studies indicate that degrading image quality can cause myopia[3-8]. A similar causation for the human eye is less clear. Human eyes recently have been found to have irregular aberrations[9-16], which degrade image quality, thereby making them candidates for myopization. We measured monochromatic aberrations in myopic and emmetropic children and adults, and found that adult emmetropes had less aberrations than either myopes or emmetropic children. These results indicate that high image quality is necessary for maintaining emmetropia.

A single lens forms an image of a distant object at its focal plane. The distance between the lens and the focal plane is the focal length, a characteristic parameter of the lens. The focal length of the human eye is determined by both the geometric curvature of corneal and lens surfaces and the refractive indices of their ocular media. In most infants, the focal length is greater than the axial length so that the focal plane lies behind the retinal plane (hyperopia). Eye growth in childhood tends to match the focal plane with the retina so as to achieve emmetropia. The match, however, is not maintained in animal experiments if image clarity is disrupted by either lid fusion[3-5] or otherwise depriving the eye of spatial information[6-8]. These manipulations cause the eye to grow too long so that the focal plane lies in front of the retina (myopia). This dependence of myopia development on image quality has been observed in various species ranging from chicken to monkey, but the underlying mechanisms are not fully understood. Although experimental manipulation on the human eye is not possible, Nature poses its own tests of this issue. The human eye is not an ideal optical system. Its defects are called aberrations and are caused by local variations in both surface curvatures and refractive indices in the cornea and the lens and/or misalignment of the optical axes of the cornea and lens relative to the visual axis of the eye. The aberrations cause the light rays passing through the pupil to divert from their ideal paths, and proportionately degrade image quality so that clearest vision can not be reached even though the focal plane matches the retina perfectly. Recent measurements in human eyes have shown that the aberrations vary substantially from one individual to another in their form and amount[9-16]. In this study we measured aberrations for 280 subjects with different ages and different refractive errors in order to demonstrate the effect of aberrations, hence image quality, on the match between the focal plane and the retina in the human eye.

Wavefront aberrations at the pupil plane have recently been used to characterize the overall effect of aberrations[9-11, 13-16]. The wavefront represents an equal-phase surface for the light rays passing the pupil at any given time, and forms a flat surface on the pupil plane if the eye is ideal. Deficiencies in the optics of the eye cause the wavefront to deviate from the ideal surface, and the degree of the wavefront deviations, or wavefront aberrations, directly depends on how the optics are flawed. We used a psychophysical ray-tracing technique with natural pupils to measure wavefront aberrations[9, 16], and used a root-mean-square (RMS) of the deviated wavefront, relative to the ideal flat wavefront as an estimate for the effect of wavefront aberrations. Subjects were divided into four groups according to their age and refractive error as shown in Table 1. Among the 280 subjects, eighteen percent are Caucasian and eighty-two percent are Chinese.

Frequency histograms of the RMS of wavefront aberrations in the worst eye for each subject indicate that every subject has RMS of wave-aberration greater than 0.5. This result means that the human eye is not perfect but suffers image degradation resulting from the deficiency in optics. Adult emmetropes, however, have the lowest mean RMS of wave-aberration which is significantly different from the means in the other groups (vs children's emmetropic group, $t=5.55$ $p<0.0001$; vs myopic adult group, $t=4.85$, $p<0.0001$; and vs myopic children's group, $t=6.45$, $p<0.0001$). They have the smallest standard deviation and it is also significantly different from the other groups (vs emmetropic children's group, $F=2.39$, $p<0.005$; vs myopic adult group, $F=8.89$, $p<0.001$; and vs myopic children's group, $F=10.72$, $p<0.001$). The highest RMS value in the adult emmetropic group is 1.62 which is exceeded by forty percent of myopic adults, 37.5% of myopic children, and 23% of emmetropic children in our sample. The results indicate that adult emmetropes suffer the least image degradation and that stronger image degradation occurs for about forty percent of myopes who have aberrations greater than all adult emmetropes.

Compared with the wave-aberrations for emmetropic children, some of whom may develop myopia later, the limited wave-aberration for adult emmetropes indicates that for the human eye to maintain emmetropia image degradation must be small. People with strong wave-aberration, who suffer strong image degradation, may fail to maintain the match between the focal plane and the retinal plane, and thereby develop myopia. These findings are in agreement with the evidence from animal studies.

It has been suggested that myopia causes aberration[15], but if the elongation of the eye in myopia generally caused optical deficiencies in the cornea and lens, we would expect all or most myopes to have more aberrations than emmetropes. But this is not true for the sixty percent of myopes who have aberrations no greater than the adult emmetropes.

Genetic contributions to myopia have long been recognized[17-19], but the underlying mechanisms are unclear. Aberrations of the eye caused by defects in the cornea and lens may be inherited. Thus aberrations causing image degradation may be one of the genetic mechanisms leading to myopia. Meanwhile, the role of near-work can not be excluded. Stronger aberrations have been reported for an accommodated eye[20-21]. Near-work would expose the eye to stronger image degradation and thus impose a higher risk of developing myopia. Besides the contribution of aberrations either inherited or near-work associated, the existence of sixty percent of myopes with less aberrations necessarily indicates a contribution from other factors on myopia development.

Small aberrations with reduced variability in adult emmetropes, as found in this study, suggest that high optical quality of the image is a necessary condition for the human eye to maintain emmetropia. Our results also suggest that severe aberrations are associated with the development of myopia. The existence of strong aberrations in myopia, which can not be corrected with available techniques, necessitates the development of new techniques for vision care in clinical practice. The results also provide important information about the optics of the human eye for designing experiments in vision research and visual instruments in the optical industry.

Methods

Apparatus. The apparatus used in this study is a three channel optical system, including a test, a reference and a pupil monitoring channel, which share the design of the subjective wavefront sensor described in a previous study[16] in principle but was changed to a computer monitor version. The test channel provides a green cross target on the retina via a movable aperture with 1 mm diameter. As the aperture is moved from trial to trial among 37 locations within the subject's natural pupil, the cross shifts its retinal location accordingly due to the aberration of the eye. The cross shifts were traced by the subject via a cursor on the monitor of a computer provided in the reference channel. The subject's pupil was monitored by a CCD camera and a monitor in the pupil-monitoring channel during the experiment and any eye movement relative to the optical axis of the system was compensated by moving a 3D translator on which the subject's head rested. In the systems there is a movable stage with two mirrors on the common pathway set as a Badel system for compensating the subject's refractive error.

Procedure. The subject's eye was first aligned to the optical system. By looking at the monitor screen via a 1 mm aperture and adjusting the Badal system to clarify the screen, the eye was at its resting state. The measurements consisted of a few practice trials and six tests, three for each eye. Each test consisted of 39 trials with the first and the last trials for the center of the pupil. The other 37 trials randomly sampled the entire pupil with a 7×7 matrix in 1 mm steps except the 12 points in the four corners. The subject's task was to align the cursor with the center of the cross and click the mouse on each trial. Each test usually lasted about 3 minutes, and the entire session took about a half hour. Data Analysis. The shifts in the cross target recorded by the computer were translated into the slope of the wavefront at the 37 pupil locations. A least square procedure was used to fit the slope measurements to the derivatives of 35 terms of the Zernike polynomial functions. The derived coefficients provide estimates of the weight of individual aberrations, and were used to reconstruct the overall wavefront at the pupil plane.

REFERENCE

1. Gwiazda, J., Thorn, F., Bauer, J & Held, RP Emmetropization and the progression of manifest refraction in children followed from infancy to puberty. Clin. Vis. Sci. 8, 337-344 (1993).
2. Mohindra, I. & Held, R. Refractions in humans from birth to five years. Documenta Ophthal. Proc. Ser. 28, 19-27 (1981).
3. Wiesel, T. N. & Raviola, E. Myopia and eye enlargement after neonatal lid fusion in monkeys. Nature 266, 66-68 (1977).
4. Wallman, J., Turkel, J. & Trachtman, J. Extreme myopia produced by modest change in early visual experience. Science 201, 1249-1251 (1978).
5. von Noorden, G. K. & Crawford, M. L. J. Lid closure and refractive error in macaque monkeys. Nature 272, 53-54 (1978).
6. Smith, E. L. III, Harwerth, R. S. Crawford, M. L. J. & von Noorden, G. K. Observations on the effects of form deprivation on the refractive status of the monkey. Invest. Ophthal. Vis. Sci. 28, 1236-1247 (1987).
7. Schaeffel, F., Glasser, A. & Howland, H. C. Accommodation, refractive error and eye growth in chickens. Vision Res. 28, 639-659 (1988).
8. Hodos, W. & Kuenzel, W. J. Retinal image degradation produces ocular enlargement in chicks. Invest. Ophthal. Vis. Sci. 25, 652-659 (1984).
9. Smirnov, M. S. Measurement of the wave aberration of the human eye. Biofizika 6, 687-703 (1961).
10. Howland, B., & Howland, H. C. Subjective measurement of high-order aberrations of the eye. Science, 193, 580-582 (1976).
11. Walsh, G., Charman, W. N. & Howland, H. C. Objective technique for the determination of monochromatic aberrations of the human eye. J. Opt. Soc. Am. A 1, 987-992 (1984).
12. Campbell, M. C., Harrison, E. M., & Simonet, P. Psychophysical measurement of the blur on the retina due to optical aberrations of the eye. Vision Res., 30, 1587-1602 (1990).
13. Liang, J., Grimm, B., Goetz, S., & Bille, S. F. Objective measurements of wave aberrations of the human eye with the use of a Hartmann-Shack wave-front sensor. J. Opt. Soc. Amer. A, 11, 1949-1957 (1994).
14. Liang, J., & Williams, D. R. Aberrations and retinal image quality of the normal human eye. J. Opt. Soc. Amer. A 14, 2873-2883 (1997).
15. Atchison, D. A., Collins, M. J., Wildsoet, C. P., Christensen, J., & Waterworth, M. D. Measurement of monochromatic ocular aberrations of human eyes as a function of accommodation by the Howland aberroscope technique. Vision Res. 35, 313-323 (1995).
16. He, J. C., Marcos, S., Webb, R. H., & Burns, S. A. Measurement of the wave-front aberration of the eye by a fast psychophysical procedure. J. Opt. Soc. Am. A 15, 2449-2456 (1999).
11. Curtin, B. J. The myopia: Basic science and clinical management. Philadelphia: Harper & Row (1985).
18. Pacella, R., McLellan, J., Grice, K., Del Bono, E, Wiggs, J. L. & Gwiazda, J. Role of genetic factors in the etiology of juvenile-onset myopia based on a longitudinal study of refractive error. Optom. Vis. Sci. 76, 381-336 (1999).
19. Zadrik, K., Satariano, W. A., Mutti D. O., Sholtz, R. I. & Adams, A. J. The effect of parental history of myopia on children's eye size. JAMA 271, 1323-1327 (1994).

20. He, J. C., Burns, S. A. & Marcos, S. Monochromatic aberrations in the accommodated human eye. *Vis. Res.* (in press).
21. Lopez-Gil, N., Ialesias, I. & Artal, P. Retinal image quality in the human eye as a function of the accommodation. *Vision Res.* 38, 2897-2907 (1998).

Acknowledgements. We thank Jinhua Feng for help in data acquisition. This work is supported by a grant from the National Eye Institute of National Institutes of Health, U.S.A., the National Natural Science Foundation of China and K. C. Wang Education Foundation of Hong Kong.

TABLE 1

Subjects' information

| | Number of Subjects | | Age (years) | | Spherical equivalent error (Diopter) |
|---|---|---|---|---|---|
| | Male | Female | Mean | Range | |
| Emmetropic Adults | 20 | 25 | 21.5 | 19-27 | 0.75 to −0.5 |
| Emmetropic Children | 45 | 35 | 15.1 | 12-17 | 0.75 to −0.5 |
| Myopic Adults | 39 | 41 | 21.4 | 19-29 | −0.6 to −9.0 |
| Myopic Children | 35 | 40 | 15.0 | 11-18 | −0.6 to −7.0 |

Figure Caption

Figure 1:
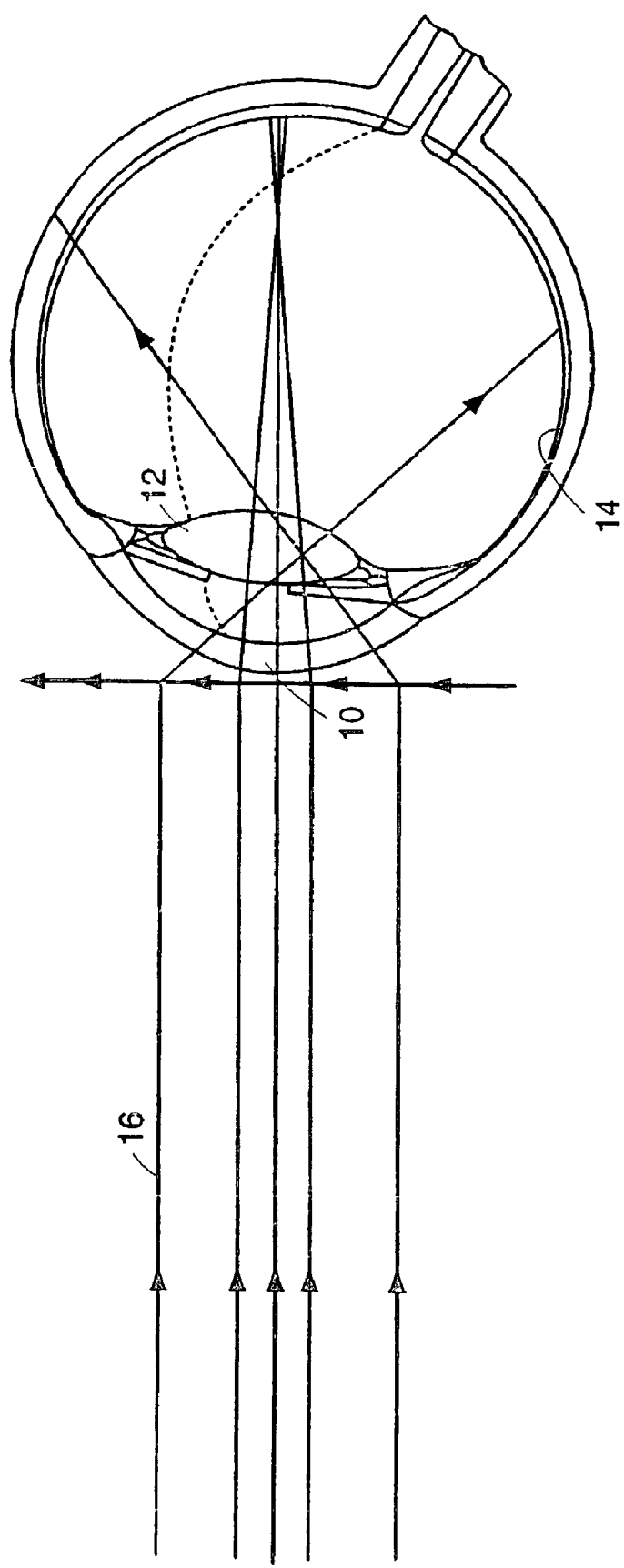
FIG. 1 shows a structure of an eye relevant to the present invention.

FIG. 1 Frequency histograms of the root-mean-square (RMS) of wavefront aberration in the human eye for 280 subjects in four groups. The number of subjects (N) and the mean RMS with standard deviation are indicated for each group.

What is claimed is:

1. A method for at least one of preventing myopia and retarding the progression of myopia, the method comprising:
    identifying a child prone to myopia on the basis of aberrations in an eye of the child;
    measuring optical aberrations in the child's eye; and
    impeding progression of myopia by correcting the optical aberrations.

2. A method according to claim 1, wherein the step of measuring includes measuring wavefront aberrations of parallel light rays entering the eye.

3. A method according to claim 1, wherein the step of measuring includes measuring deviations at the retina of parallel light rays entering the eye.

4. A method according to claim 1, wherein the step of measuring includes measuring deviations at the pupil of parallel light rays entering the eye.

5. A method according to claim 1, wherein the step of measuring includes providing a multi-channel optical system.

6. A method according to claim 5, further comprising:
    moving an aperture to multiple positions with respect to the pupil of the eye;
    recording alignment parameters of features for each aperture position at least one optical distance; and
    solving a system of equations to derive a set of aberration constants based on the alignment parameters.

7. A method according to either of claim 5 or 6, wherein the step of measuring includes detecting first and higher order astigmatism.

8. A method according to either of claim 5 or 6, wherein the step of measuring includes detecting at least one of first and higher order coma, spherical aberrations and other aberrations.

9. A method for at least one of preventing myopia and retarding the progression of myopia, the method comprising:
    screening for higher order aberrations in an eye of a child;
    measuring the aberrations in the eye; and
    impeding progression of myopia by correcting the aberrations.

10. A method according to claim 9, wherein the step of screening includes measuring visual acuity.

11. A method according claim 9, wherein the step of screening includes measuring blur sensitivity.

12. A method according to claim 10, wherein visual acuity is measured with a psycho-physical test.

13. A method according claim 11, wherein blur sensitivity is measured with a psycho-physical test.

14. A method according to either of claim 1 or 9, wherein the step of correcting includes providing an optical device.

15. A method according to either of claim 1 or 9, wherein the step of correcting includes providing at least one optical lens.

16. A method according to either of claim 1 or 9, wherein the step of correcting includes providing at least one contact lens.

17. A method according to either of claim 1 or 9, wherein the step of correcting includes altering an optical surface in the eye.

18. A method according to either of claim 1 or 9, wherein the step of correcting includes performing corneal surgery.

19. A method according to either of claim 1 or 9, wherein the step of correcting includes providing intra-ocular implants.

20. A method according to either of claim 1 or 9, wherein the step of correcting includes providing high illumination levels to reduce the eye's pupil.

21. A method according to either of claim 1 or 9, wherein the step of correcting includes providing adaptive optics.

22. A method according to claim 21, wherein the adaptive optics include deformable mirrors.

23. A method according to claim 21, wherein the adaptive optics include at least one system of multiple lenslettes.

24. A method according to claim 21, wherein the adaptive optics include micro-mirror electro-machined components.

25. A method according to claim 21, wherein the adaptive optics include optically addressed liquid crystal spatial light modulators.

26. A method according to claim 21, wherein the adaptive optics include membrane mirrors.

27. A method according to claim 21, wherein the adaptive optics include piezoelectric bi-morph mirrors.

28. A method according to claim 21, wherein the adaptive optics are miniaturized so as to be wearable on the face of a person.

29. A method according to claim 21, wherein the adaptive optics produce periods of clear vision.

30. A method according to claim 9, wherein the step of screening includes measuring contrast sensitivity.

31. A method according to claim 30, wherein contrast sensitivity is measured with a psycho-physical test.

32. A method according to claim 9, wherein the step of screening includes measuring depth of focus.

33. A method according to either of claim 1 or 9, wherein the step of measuring includes measuring wavefront aberrations using an aberrometer.

34. A method according to either of claim 1 or 9, wherein the step of measuring includes measuring wavefront aberrations using a Shack-Hartman wavefront sensor.

* * * * *